United States Patent [19]
Gerblinger et al.

[11] Patent Number: 5,505,073
[45] Date of Patent: Apr. 9, 1996

[54] SENSOR HAVING A SENSOR ELEMENT ARRANGED IN A HOUSING

[75] Inventors: Josef Gerblinger, Wertingen; Uwe Lampe, Buxtehude; Hans Meixner, Haar, all of Germany

[73] Assignee: Siemens Aktiengesellschaft, Munich, Germany

[21] Appl. No.: 279,038

[22] Filed: Jul. 22, 1994

[30] Foreign Application Priority Data

Jul. 22, 1993 [DE] Germany ............. 43 24 659.1

[51] Int. Cl.⁶ .................. G01N 7/00; G01N 33/22
[52] U.S. Cl. ........................................ 73/31.05
[58] Field of Search .................. 73/23.31, 23.32, 73/31.05; 204/422, 424, 426, 428; 55/434, 307, 385.3, 462, 465; 338/34

[56] References Cited

U.S. PATENT DOCUMENTS

| | | | |
|---|---|---|---|
| 2,932,966 | 4/1960 | Grindell | 73/23.31 |
| 3,776,208 | 12/1973 | Stumpp. | |
| 4,115,229 | 9/1978 | Capone | 73/23.31 |
| 4,339,318 | 7/1982 | Tanaka et al. | 204/428 |
| 4,492,614 | 1/1985 | Welsh. | |
| 4,535,316 | 8/1985 | Wertheimer et al. | |
| 4,597,850 | 7/1986 | Takahasi et al. | 73/31.05 |
| 4,742,711 | 5/1988 | Porth et al. | |
| 4,903,481 | 2/1990 | Schuster et al. | 204/428 |
| 4,916,934 | 4/1990 | Nagata et al. | |
| 4,944,861 | 7/1990 | Reber | 204/428 |
| 5,251,470 | 10/1993 | Lampe et al. | |

FOREIGN PATENT DOCUMENTS

| | | |
|---|---|---|
| 0158256 | 10/1985 | European Pat. Off. . |
| 0222987 | 5/1987 | European Pat. Off. . |
| 0464243 | 1/1992 | European Pat. Off. . |
| 0464244 | 1/1992 | European Pat. Off. . |
| 0175077 | 3/1992 | European Pat. Off. . |
| 0503295 | 9/1992 | European Pat. Off. . |
| 3500088 | 7/1986 | Germany . |
| 269046 | 10/1989 | Japan ........................ 204/424 |

*Primary Examiner*—Hezron E. Williams
*Assistant Examiner*—Daniel S. Larkin
*Attorney, Agent, or Firm*—Hill, Steadman & Simpson

[57] ABSTRACT

A sensor assembly for sensing gaseous or fluid medium such as sensing oxygen within exhaust gas of an automobile. The assembly provides a sensor element within a housing mounted within a S-shaped flow channel between a medium entry aperture and exit aperture. A shield is provided upstream of the sensor in a flow direction of the medium. The arrangements provide for a laminar flow across the sensor element causing reduced deposits on the surface of the sensing element for a more accurate sensor and a longer service life of the sensor element.

14 Claims, 8 Drawing Sheets

SENSOR HAVING A SENSOR ELEMENT ARRANGED IN A HOUSING

BACKGROUND OF THE INVENTION

The operating behavior of an internal combustion engine is critically dependent on the quality of the mixture preparation or carburation. Thus, the emission of harmful substances and the fuel consumption of an engine can be substantially reduced by a mixing of the fuel to the intake air that is adapted to the respective operating condition. This is especially true for a motor vehicle internal combustion engine equipped with a controlled 3-way catalyst. The catalyst serving the purpose of reducing the pollutant emission, however, operates with high efficiency only within an extremely narrow range of air ratios. In order to assure a maximum degree of conversion, the air/fuel ratio therefore must only deviate from a rated value representing the respective optimum by a few percent in every operating condition of the engine.

The probes on the basis of zirconium oxide that become ion-conductive at higher temperatures and that serve the purpose of determining the air ratio $\lambda$ respond comparatively slowly to changes of the partial oxygen pressure in the exhaust gas. They are therefore not suitable for cylinder-selective $\lambda$ control and shall be advantageously replaced in the future by metal oxide sensors whose response time amounts to only a few milliseconds. These gas sensors manufactured in planar technology usually have a base member composed of a ceramic material on whose surface two interdigital electrodes and a metal oxide layer (for example, $SrTiW_3$, $CeO_2$ or $Ga_2O_3$) that conductively connects the electrodes are applied. A resistor element present at the back side of the base member allows the active heating of the gas sensor. When oxygen flows over the thermally activated metal oxide, then the resistance or, respectively, conductance thereof changes reversibly due to complicated adsorption process at the oxide surface. The oxygen concentration in the exhaust gas can therefore be determined in a simple way by a measurement of resistance or, respectively, conductance.

Deposits on the surface of the metal oxide layer which is only a few $\mu m$ thick can substantially influence the gas-sensitive and electrical properties thereof. Sensors on the basis of semiconductive metal oxides are therefore arranged in a housing in order to keep the particles present in the exhaust gas of an internal combustion engine away from the $O_2$-sensitive regions. The particles that deteriorate the sensor function derive from the additives and the contaminants of the fuels (lubricating oil, benzene, etc.) or, respectively, arise during operation of the engine due to friction. Typically, they have a size of approximately 1–2 $\mu m$ and, among other things, are composed of iron oxides.

U.S. Pat. No. 4,916,934 discloses an oxygen detector composed of a planar sensor element and of a cylindrical housing. In order to prevent a direct flow against the oxygen-sensitive layer, the sensor element and the gas entry apertures present in the generated surface of the housing are arranged in different planes. The baffles respectively allocated to the entry apertures are intended to intercept the particles present in the exhaust gas and to produce a circular gas flow in the inside of the housing.

The cylinder housing for a fast exhaust gas sensor disclosed by EP-A-0 503 295 likewise comprises a plurality of slot-shaped gas entry apertures whose edges overlap louver-like. Since the slots act as particle traps, deposits on the sensitive sensor layer are effectively suppressed.

In order to prevent deposits in the apparatus for detecting chlorine and chlorine-containing compounds disclosed by DE 35 00 088 A1, only test gases that contain no particles and liquid drops are supplied to the solid electrolyte that serves as sensor element. The largely non-porous solid electrolyte that is incorporated sealed in a housing separates two respectively cylindrical chambers, whereby the one chamber is filled with the gas to be measured and the other chamber is filled with a reference gas. Two respective housing bores that enable the gas exchange discharge into the chambers.

SUMMARY OF THE INVENTION

A goal of the present invention is to create a sensor that can be exposed for a longer time to a particle-loaded gas or fluid stream without being damaged. The sensor housing should not impede the gas or, respectively, fluid exchange with the sensor element and should lengthen the service life of the sensitive regions. These objects are inventively achieved by a sensor having a sensor element and a housing for accepting the sensor element, whereby the housing is equipped with an entry aperture and with an exit aperture for a gaseous or fluid medium. The housing has a curved flow channel connecting the entry aperture to the exit aperture and the sensor element is arranged in the flow channel downstream of a curved portion of the channel, in the flow direction.

Advantageously, the flow channel is curved in a S-shape. The flow channel can be provided with a first section open to the entry aperture and a second section discharging into the exit aperture with the sensor element arranged in a middle section that connects the respectively curved first and second channel sections. The first and second sections of the flow channel each can comprise a curvature of approximately 90°. The middle section connecting the first and second channel section can comprise a circular cross section. The sensor element is preferably arranged in a region of the flow channel through which the flow is largely laminar. The sensor element can provide a planar structure aligned such that the medium flows parallel to the surface of the sensor element. A shield can be arranged immediately in front of the sensor element in the flow direction. The end faces of the shield and of the sensor element are of approximately the same size. The shield can taper in the flow direction.

The housing is preferably composed of an upper and lower part whereby the upper part contains the entry aperture, the first section of the flow channel and the shield, and the sensor element is secured to the lower part of the housing and projects into the upper part. The entry aperture and the exit aperture can be fashioned slot-like. The housing can provide further entry and exit apertures respectfully discharging into the flow channel.

An advantage that can be achieved with the invention is especially that nearly particle-free gas flows largely laminarly and parallel to the surface of the planar sensor element. Since no turbulence of the exhaust gas packets generated by an internal combustion engine occurs in the channel of the housing, the sensor equipped with a fast, oxygen-sensitive element can be utilized as $\lambda$-probe for the cylinder-selective regulation of the air ratio.

BRIEF DESCRIPTION OF THE DRAWINGS

FIG. 12b is a sectional view taken generally along line XIIb—XIIb of FIG. 12a;

FIG. 13b is a sectional view taken generally along line XIIIb—XIIIb of FIG. 13a;

FIG. 13c is a sectional view taken generally along line XIIIc—XIIIc of FIG. 13a;

FIG. 13d is a sectional view taken generally along line XIIId—XIIId of FIG. 13a;

FIG. 14a is a plan view of a ceramic plate that terminates the lower part of the sensor housing shown in FIG. 13a;

FIG. 14b is a sectional view taken generally along line XIVb—XIVb of FIG. 14a;

FIG. 14c is a enlarged partial plan view of a central region "Z" shown in FIG. 14a;

DETAILED DESCRIPTION OF THE PREFERRED EMBODIMENTS

Figure 1:
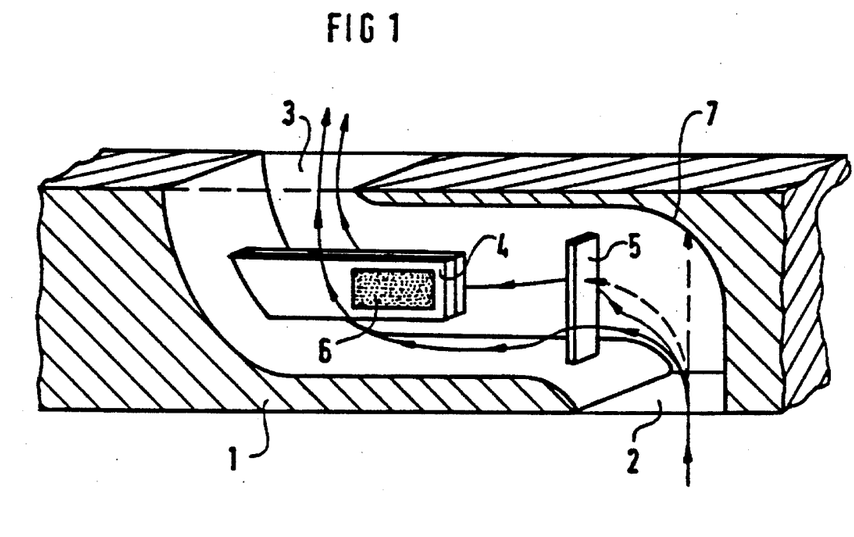
FIG. 1 is a schematic perspective cut-away view of a structure of a gas sensor of the invention.

The steel housing 1 of the gas sensor schematically shown in FIG. 1 is similar in structure to a tobacco pipe. It comprises a flow channel exhibiting two curved sections and a cylindrical middle part, this flow channel connecting the slot-shaped gas entry aperture 2 to the likewise slot-shaped gas exit aperture 3. The planar sensor element 4 is arranged behind a shield such as a metal ridge 5 as viewed in flow direction and is secured in a bore (not shown) of the housing 1. Since the spacing between the ridge 5 and the sensor element 4 preferably amounts to only a few millimeters, no eddies can form in the interspace. The gas to be measured therefore flows largely laminar and parallel to the surface of the gas-sensitive metal oxide layer 6 in the middle part of the channel. In order to also keep the flow turbulence-free in the back part of the channel, the end section discharging into the gas exit aperture 3 is executed curved. The gas stream experiences a deflection of approximately 90° here, so that the gas emerging from the housing 1 and the gas to be measured that enters into the housing flow in the same direction.

That section of the channel open into the gas entry aperture 2 is likewise curved and deflects the gas stream by approximately 90° in the direction of the sensor element 4. Since the heavier particles present in the gas to be measured cannot follow the curvature of the channel due to their inertia, they impinge the channel wall in the region 7 and remain adhering thereto. The lighter-weight particles potentially also entrained in the deflected gas stream strike the metal ridge 5 arranged immediately in front of the sensor 5 in flow direction or, respectively, are conducted past the sensor element 4 parallel thereto due to the gas flow that forms following the ridge 5.

In order to assure that the sensor element 4 is flooded with exhaust gas largely turbulence-free, this sensor element preferably has a planar structure and preferably should be aligned with respect to the ridge in the way shown in FIG. 1. The gas to be measured then particularly flows parallel to the gas-sensitive layer 6 when the end faces of the ridge 5 and of the sensor element 4 are of approximately equal size and when the ridge 5 is implemented as a member that tapers in flow direction.

Figure 2:
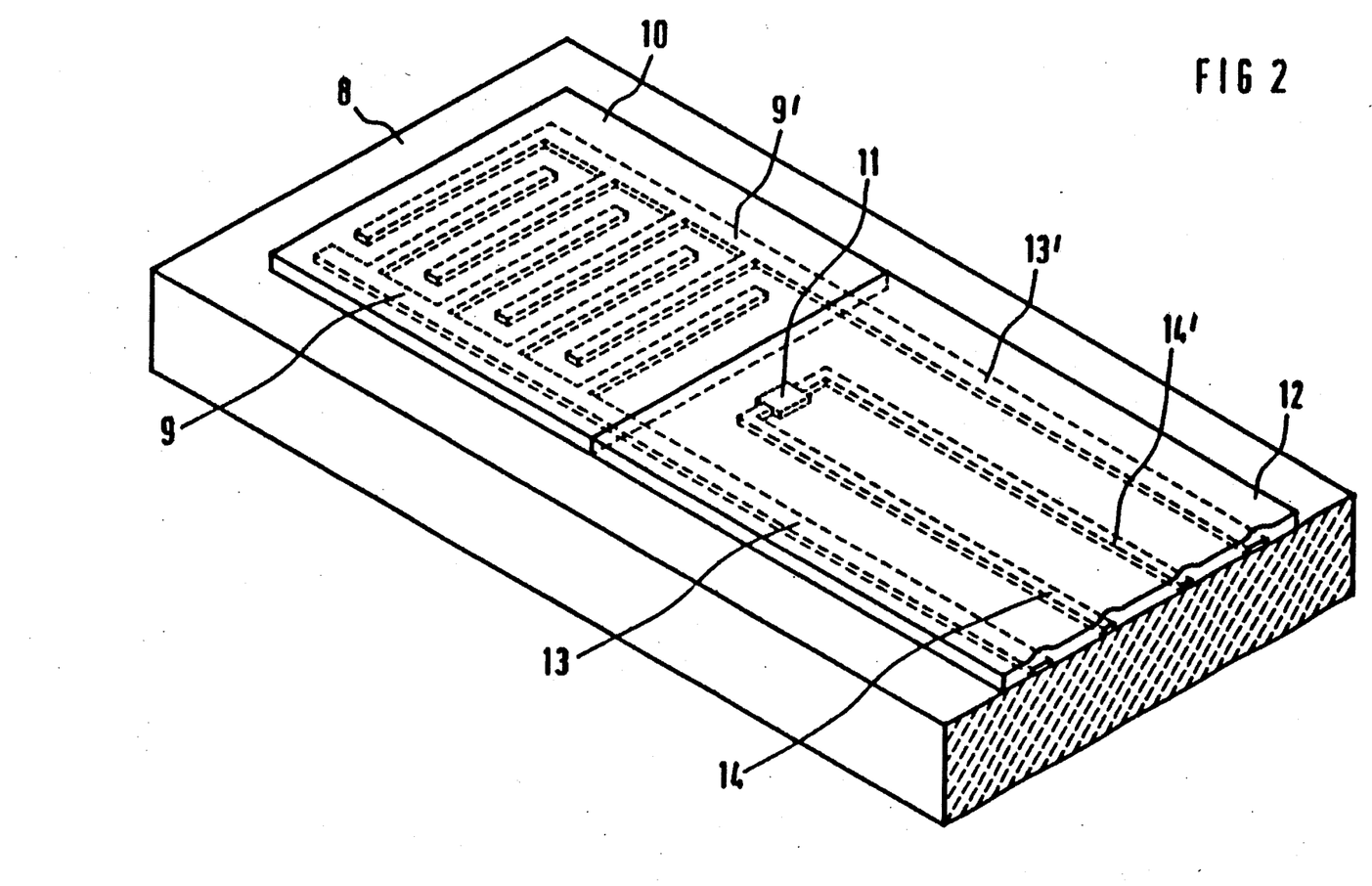
FIG. 2 is a perspective view of an exemplary embodiment of a planar sensor element.
Figure 4:
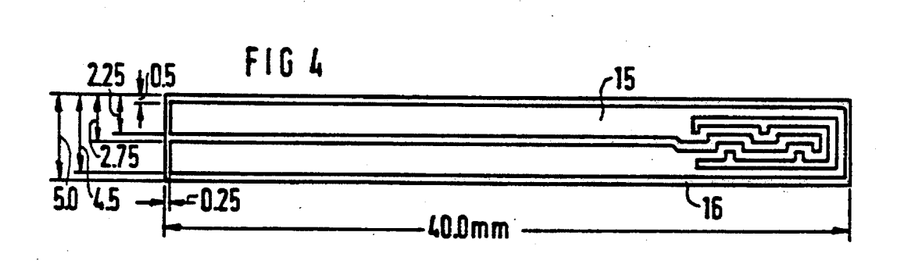
FIG. 4 is a sectional view of a heating element of the gas sensor of FIG. 3.
Figure 5:
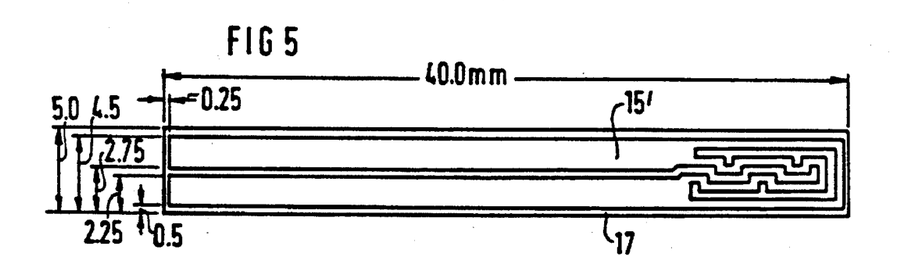
FIG. 5 is a sectional view of a second heating element of the gas sensor of FIG. 3.

The sensor element for measuring the partial pressure of oxygen that is schematically shown in FIG. 2 is similar in structure to the detectors disclosed by EP-A-0 464 243 and 0 464 244. It has a substrate 8 composed, for example, of magnesium oxide, silicon oxide ore aluminum oxide, two platinum electrodes 9 and 9' forming an interdigital structure, a strontium or barium titanate layer 10 that is approximately 1–2 mµ thick and covers these electrodes, and a temperature sensor 11 being arranged on the surface of this substrate 8. The passivation layer of glass or silicon oxide referenced 12 shields the leads 13 and 13' or, respectively 14 and 14' respectively allocated to the electrodes 9 and 9' and to the temperature sensor 11 from the oxygen present in the gas to be measured. A resistive layer of platinum arranged at the back side of the substrate 8 is employed as heating element and, for example, can comprise the structure shown in FIGS. 4 or 5.

Figure 3:
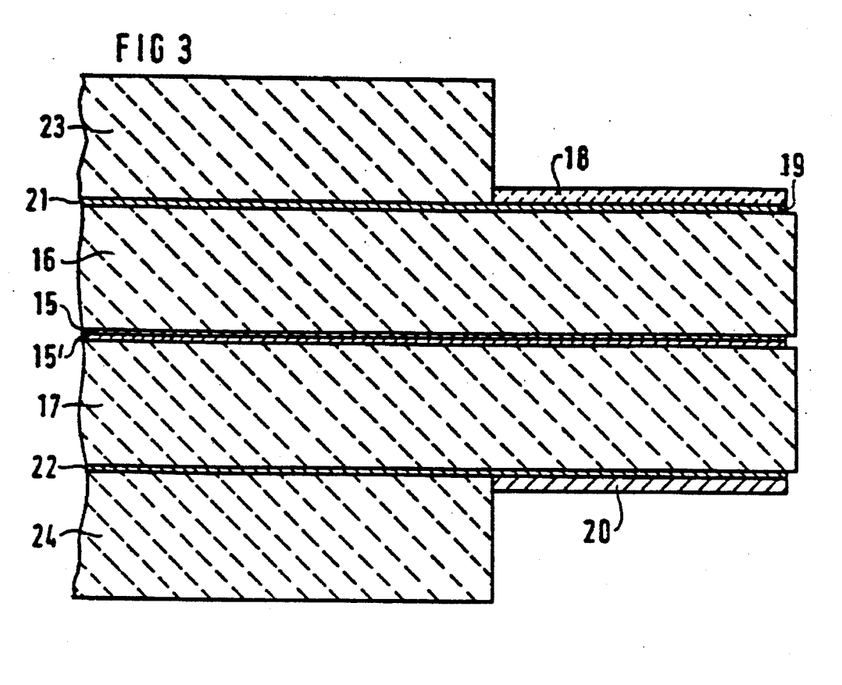
FIG. 3 is a sectional view of a second exemplary embodiment of a planar sensor element.
Figure 6:
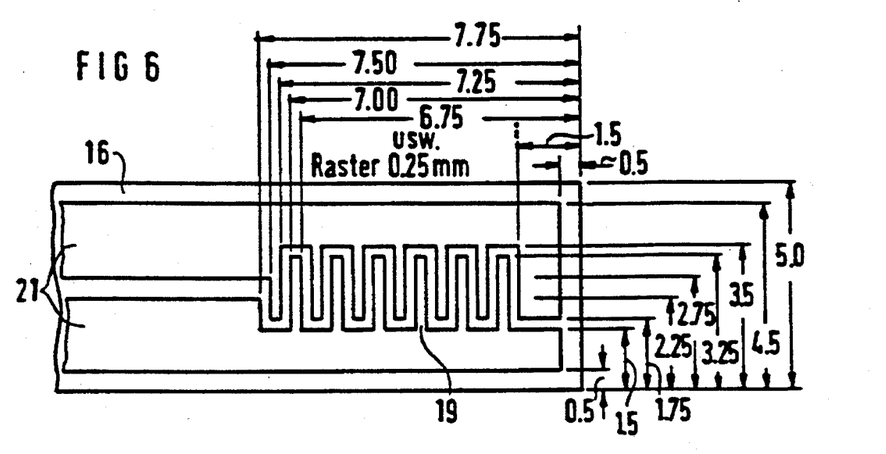
FIG. 6 is a partial sectional view of an electrode for contacting the gas-sensitive metal oxide layer of the sensor element of FIG. 3.
Figure 7:
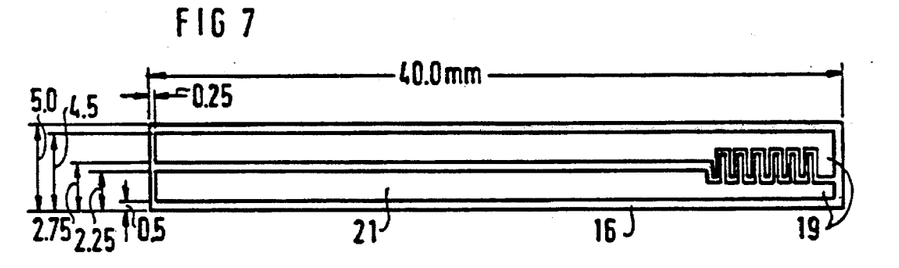
FIG. 7 is a sectional view of the electrode of FIG. 6 for contacting the gas-sensitive metal oxide layer of the sensor element of FIG. 3.
Figure 8:
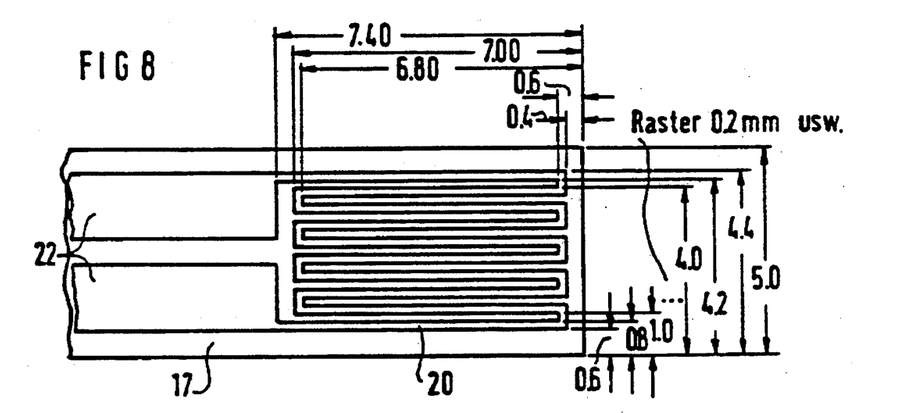
FIG. 8 is a partial sectional view of an exemplary embodiment of a temperature sensor.
Figure 9:
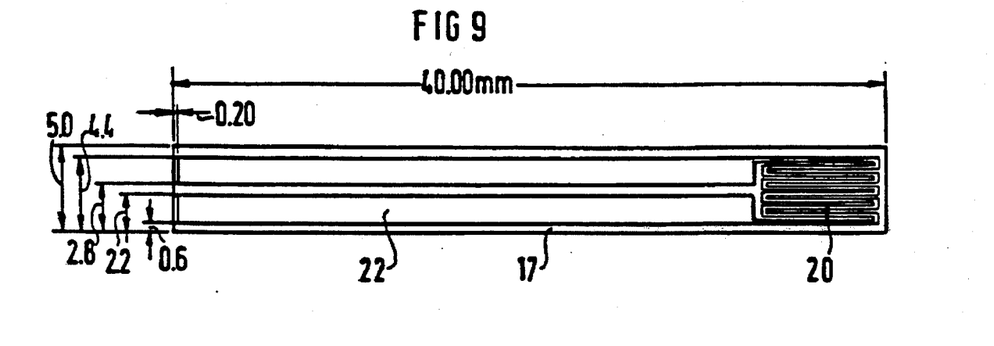
FIG. 9 is a sectional view of the temperature sensor of FIG. 8.

FIG. 3 shows a section through the head of a sensor element especially suitable for integration in the pipe housing 1. In this embodiment, the platinum layers referenced 15 or, respectively 15' and shown in FIGS. 4 and 5 serve as heating element. They are applied onto the $Al_2O_3$ substrate 16 and 17 with a silkscreening process. The oxygen-sensitive $SrDiO_3$ or $BaTiO_3$ layer 18 and the interdigital electrodes 19 or, respectively, the temperature sensor 20 likewise composed of platinum as well as the terminal electrodes 21 or, respectively, 22 thereof are arranged at those surfaces of the substrate 16 or, respectively, 17 lying respectively opposite the platinum layers 15 and 15'. Advantageous geometries for the electrodes 19 that contact the sputtered-on metal oxide 18 and for the temperature sensor 20 may be found in FIGS. 6 and 7 or, respectively, 8 and 9, whereby FIGS. 6 and 8 each respectively show the electrode structure in the region of the sensor head. The $Al_2O_3$ layers references 23 and 24 in FIG. 3 are intended to shield the leads 21 or, respectively, 22 respectively allocated to the interdigital electrodes 19 and to the temperature sensor 20 from oxygen of the measured gas that flows around the sensor.

Figure 10:
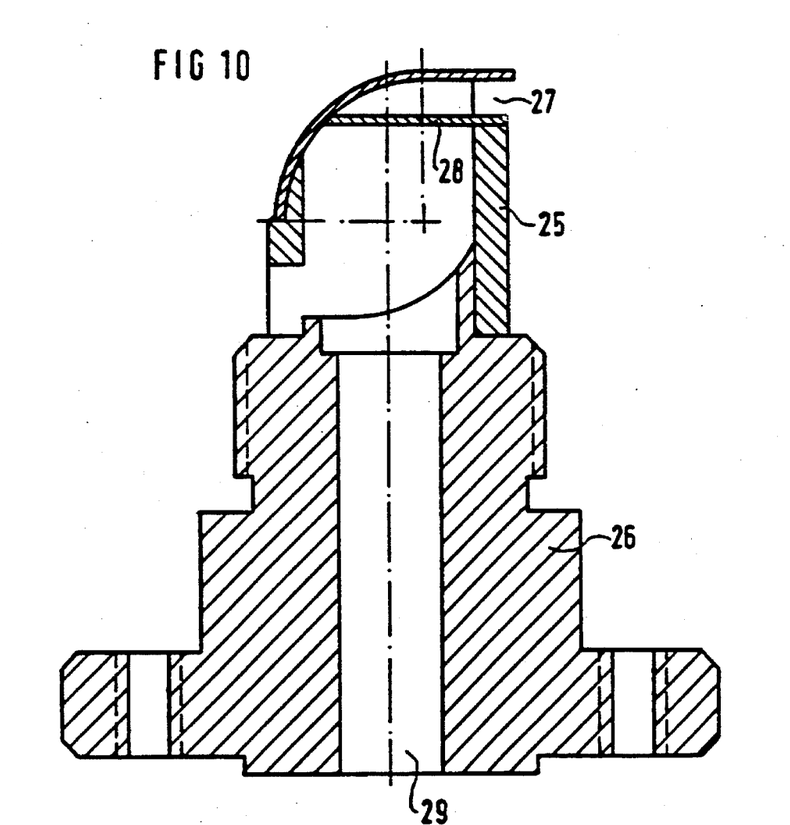
FIG. 10 is a sectional view of an exemplary embodiment of the sensor housing.
Figure 11A:
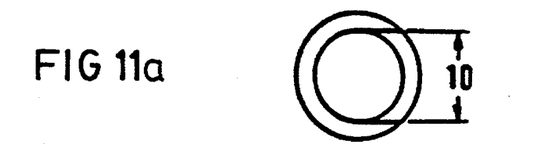
FIG. 11a is a top view of a head member of the sensor housing of FIG. 10.
Figure 11B:
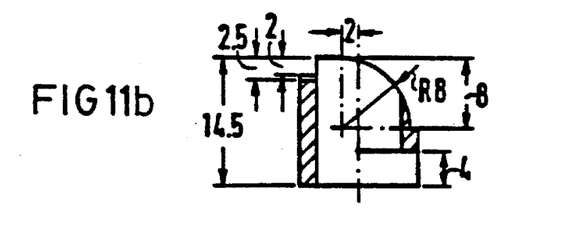
FIG. 11b is a sectional view of a head member of the sensor housing of FIG. 10.
Figure 11C:
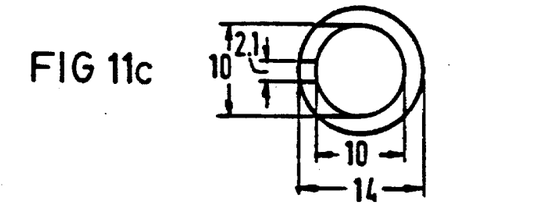
FIG. 11c is a bottom view of a head member of the sensor housing of FIG. 10.
Figure 12A:
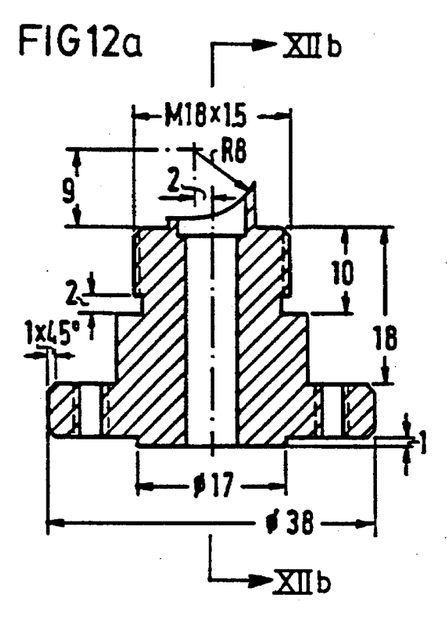
FIG. 12a is a sectional view of a base member of the sensor housing of FIG. 10.
Figure 12B:
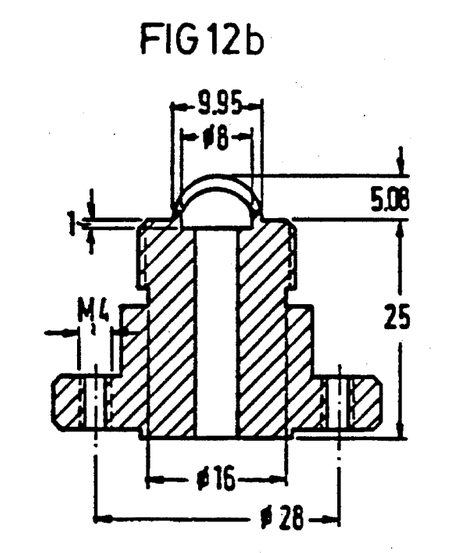
Figure 13A:
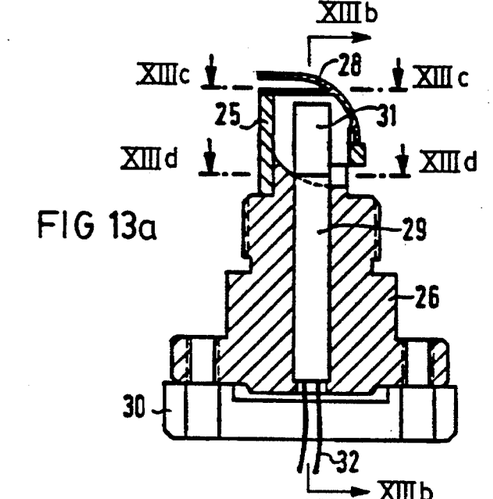
FIG. 13a is a sectional view through the housing equipped with the sensor element.
Figure 13B:
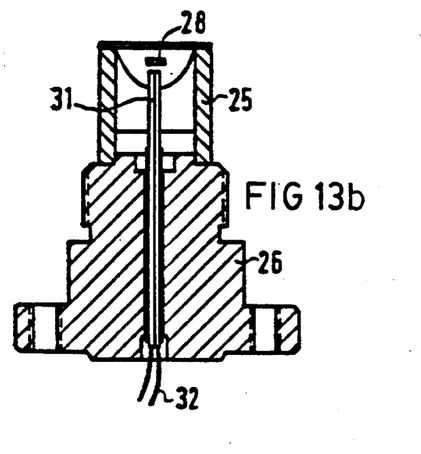
Figure 13C:
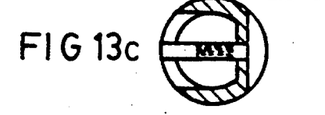
Figure 13D:
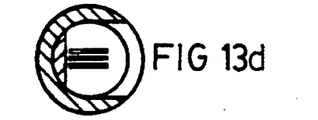

The sensor housing shown in FIG. 10 is composed of two parts 25/26, whereby the housing head 25 is fabricated, for example, of Inconel and contains the gas entry aperture 27 and the ridge 28 and is secured to the base member 26 that is equipped with a bore 29 for accepting the sensor element. Before the two parts 25 and 26 shown in section in FIGS. 11a,b,c and 12a,b are welded, the sensor element whose outside surfaces are coated with a ceramic adhesive is inserted into the bore 29 of the base member 26. Care is thereby to be exercised to see that no contaminants due to the ceramic adhesive occur in the region of the sensor head and to see that the glued locations terminate shape-identically with the rounded portions of the housing head 25. The hardening of the ceramic adhesive ensues during a temperature process at 200° C. that lasts approximately 20 minutes.

Figure 14A:
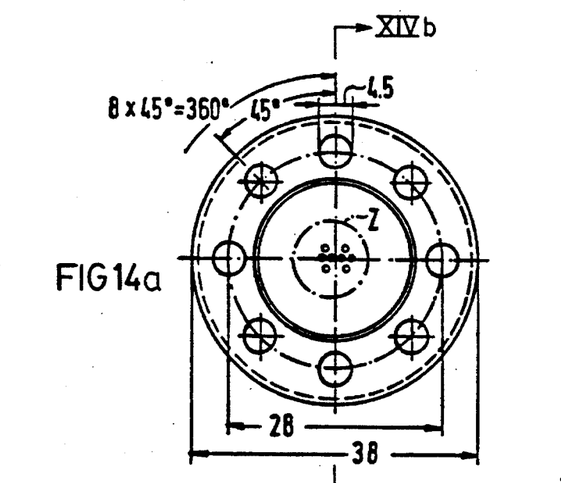
Figure 14B:
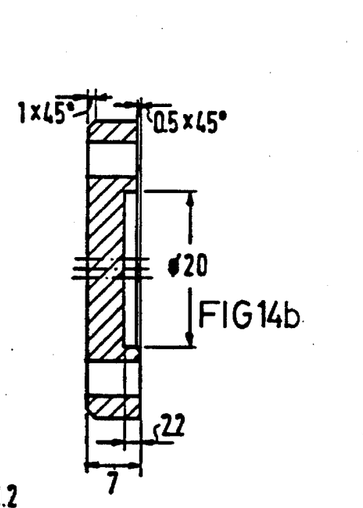
Figure 14C:
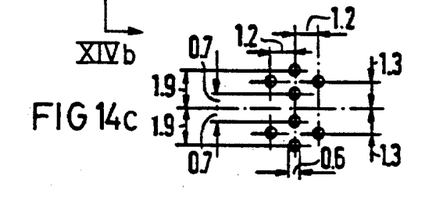

FIG. 13a–d shows the completely assembled gas sensor. The ceramic (Makor) plate 30 that terminates the glued bore 29 of the lower housing part 26 is also shown (also see FIG. 14a–c). It contains a total of eight ducts through which the platinum wires 32 required for contacting the sensor element 31 are conducted to the outside.

Figure 15A:
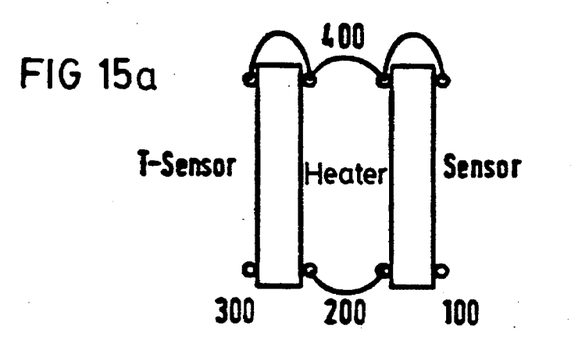
FIG. 15a and 15b are schematic view of the interconnection and the terminals of the sensor component.
Figure 15B:
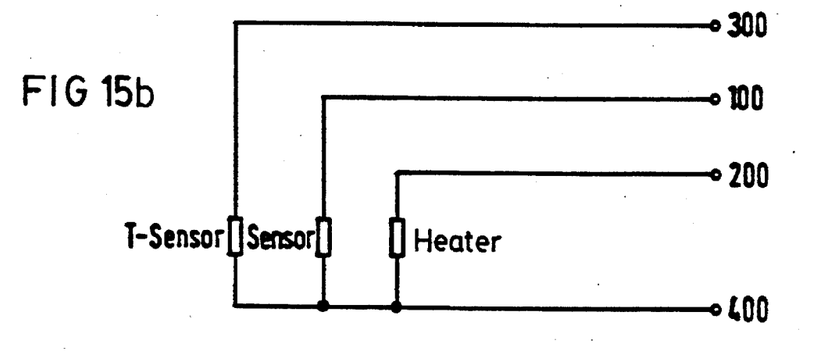

In order to reduce the plurality of electrical terminals from 8 to 4, the grounds of the sensor element, of the temperature sensor and of the two heating elements are combined in one terminal 400 (see FIG. 15a,b). While the filament voltage is adjacent between the terminals 200 and 400, the sensor signal representing the partial oxygen pressure can be taken between the terminals 100 and 400 and the resistance of the temperature sensor can be taken between the terminals 300 and 400. For insulating the platinum wires, these are fused, for example, into a glass ceramic composed of silicon, magnesium or boron oxides.

Figure 16:
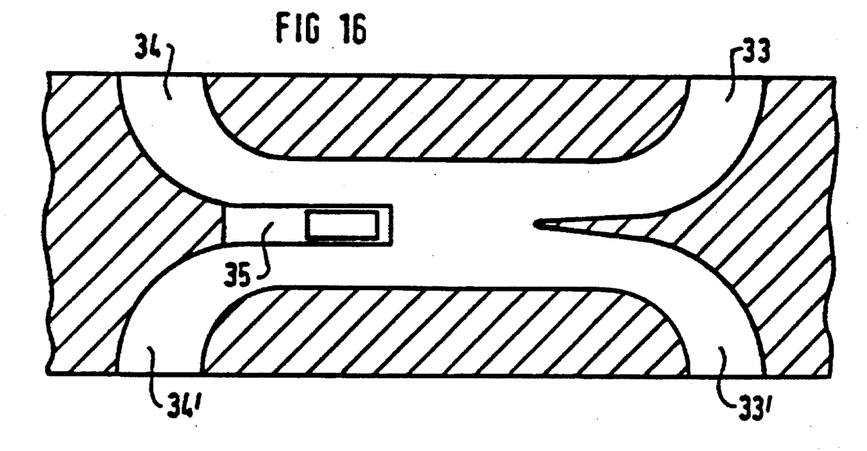
FIG. 16 is a sectional view of a second exemplary embodiment of a sensor housing comprising a plurality of gas entry and gas exit apertures.

The invention, of course, is not limited to the exemplary embodiments that have been set forth. It is thus possible without further ado to provide a plurality of gas entry and gas exit apertures 33, 33' or, respectively 34, 34' that are preferably symmetrically arranged relative to the longitudinal axis of the sensor housing and to connect these gas entry and exit apertures to the main channel accepting the sensor element 35 with curved side channels (see FIG. 16).

The sensor element is extremely well-protected against deposits even without employing a ridge. Due to the largely turbulence-free flow in the channel, the lighter-weight particles still entrained in the deflected gas to be measured have no or only very low transversal velocity components in the direction of the sensitive layer. They are therefore conducted past the sensor element very quickly and are conveyed out of the housing together with the gas that has been measured. An accumulation of particles in the inside of the housing often observed in known systems is prevented.

The above-described principle of protecting a sensor element from particle entrained in a gas stream, of course, can also be employed for fluids.

Although the present invention has been described with reference to a specific embodiment, those of skill in the art will recognize that changes may be made thereto without departing from the scope and spirit of the invention as set forth in the appended claims.

The invention claimed is:

1. A sensor for a gaseous or fluid medium, comprising:
   a planar sensor element;
   a housing accepting said sensor element and having an admission opening and a discharge opening for a gaseous or fluid medium;
   a flow channel connecting the admission opening and the discharge opening, whereby the flow channel is curved such that the medium is deflected at most twice by respectively approximately 90° and the medium entering into the housing and the medium departing the housing flow in the same direction; and said planar sensor element is arranged in the flow channel behind a curvature following the admission opening and is aligned such that the medium and the potentially entrained particles flow parallel to a surface of the sensor element.

2. The sensor according to claim 1, wherein said flow channel comprises an S-shaped curvature between said admission opening and said discharge opening.

3. The sensor according to claim 1, wherein said flow channel comprises a middle section between 90° deflections, said sensor element arranged in said middle section.

4. The sensor according to claim 3, wherein said middle section of said flow channel comprises a circular cross section.

5. The sensor according to claim 1, wherein said sensor element is arranged in a region of said flow channel, and said flow channel is adapted and arranged to produce a laminar flow of said medium through said region.

6. The sensor according to claim 1, further comprising a shield arranged in said flow channel upstream of said sensor element in flow direction of said medium.

7. The sensor according to claim 6, wherein said shield comprises end faces and said sensor element comprises end faces, said end faces of said shield and said sensor element laterally limit widths of said shield and said sensor element with respect to the flow direction of said medium, said shield and said sensor element being approximately of equal widths.

8. The sensor according to claim 6, wherein said shield tapers in the flow direction of said medium.

9. The sensor according to claim 1, wherein said housing comprises an upper and a lower part, wherein said admission opening and a first curved portion of said flow channel are located in said upper part, and said sensor element is secured to the lower part of the housing and projects into the upper part.

10. The sensor according to claim 9, wherein said admission opening and said discharge opening are each fashioned having a slot-like shape.

11. The sensor according to claim 1, wherein said housing further comprises an additional entry aperture and an additional exit aperture flow connected to said flow channel.

12. The sensor according to claim 1, wherein said flow channel comprises:
   a first curved portion adjacent said admission opening;
   a second curved portion adjacent said discharge opening;
   a middle section between said first curved portion and said second curved portion, said sensor element arranged in said middle section; and
   wherein said housing comprises an upper part and a lower part, wherein said admission opening and said first curved portion of said flow channel are located in said upper part, and said sensor element is secured to the lower part of the housing and projects into the upper part.

13. The sensor according to claim 12, wherein said first curved portion, said middle section and said second curved portion form an S-shape.

14. The sensor according to claim 13, further comprising a shield arranged in said flow channel upstream of said sensor element and aligned in the flow channel with said sensor element in the flow direction of said medium, said shield having a width approximately the same as said sensor element.

* * * * *